(12) United States Patent
Kontomaris et al.

(10) Patent No.: US 10,385,247 B2
(45) Date of Patent: Aug. 20, 2019

(54) USE OF (2E)-1,1,1,4,5,5,5-HEPTAFLUORO-4-(TRIFLUOROMETHYL)PENT-2-ENE IN HIGH TEMPERATURE HEAT PUMPS

(71) Applicant: THE CHEMOURS COMPANY FC, LLC, Wilmington, DE (US)

(72) Inventors: Konstantinos Kontomaris, Wilmington, DE (US); Robert Daniel Lousenberg, Wilmington, DE (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 71 days.

(21) Appl. No.: 15/506,639

(22) PCT Filed: Sep. 3, 2015

(86) PCT No.: PCT/US2015/048234
§ 371 (c)(1),
(2) Date: Feb. 24, 2017

(87) PCT Pub. No.: WO2016/048613
PCT Pub. Date: Mar. 31, 2016

(65) Prior Publication Data
US 2017/0275514 A1    Sep. 28, 2017

Related U.S. Application Data

(60) Provisional application No. 62/053,955, filed on Sep. 23, 2014.

(51) Int. Cl.
| | | |
|---|---|---|
| C09K 5/04 | (2006.01) |
| C07C 21/18 | (2006.01) |
| F04D 17/12 | (2006.01) |
| F25B 30/02 | (2006.01) |
| F28D 15/02 | (2006.01) |

(52) U.S. Cl.
CPC ............... C09K 5/04 (2013.01); C07C 21/18 (2013.01); C09K 5/045 (2013.01); F04D 17/12 (2013.01); F25B 30/02 (2013.01); F28D 15/02 (2013.01); C09K 2205/126 (2013.01); C09K 2205/24 (2013.01); Y02B 30/52 (2013.01); Y02P 20/124 (2015.11)

(58) Field of Classification Search
CPC .... C09K 5/045; C09K 5/04; C09K 2205/126; F25B 21/02; F01K 25/00; F01K 7/32
USPC ..... 252/67, 68, 69; 62/597, 324.1; 60/641.1, 60/516, 643
See application file for complete search history.

(56) References Cited

U.S. PATENT DOCUMENTS

| 7,959,828 B2 | 6/2011 | Nappa et al. | |
|---|---|---|---|
| 2006/0010872 A1* | 1/2006 | Singh | C09K 5/045 60/671 |
| 2006/0242985 A1* | 11/2006 | Leck | B60H 1/3223 62/323.1 |
| 2006/0245944 A1 | 11/2006 | Leck et al. | |
| 2007/0105738 A1 | 5/2007 | Nappa et al. | |
| 2007/0108403 A1 | 5/2007 | Sievert et al. | |
| 2007/0203046 A1 | 8/2007 | Minor et al. | |
| 2010/0154419 A1* | 6/2010 | Kontomaris | C09K 5/047 60/645 |
| 2010/0263380 A1* | 10/2010 | Biederman | F01K 23/065 60/651 |
| 2011/0041530 A1 | 2/2011 | Mouli et al. | |
| 2012/0216551 A1 | 8/2012 | Minor et al. | |
| 2013/0104548 A1* | 5/2013 | Kontomaris | C09K 5/045 60/651 |
| 2013/0104575 A1 | 5/2013 | Kontomaris | |
| 2016/0178254 A1* | 6/2016 | Nishiguchi | C09K 5/044 62/115 |
| 2017/0306205 A1* | 10/2017 | Kontomaris | C09K 5/045 |

FOREIGN PATENT DOCUMENTS

| WO | 2008/027513 A2 | 3/2008 | |
|---|---|---|---|
| WO | WO-2018165623 A1 * | 9/2018 | A62D 1/0057 |

OTHER PUBLICATIONS

CAS No. 1894231-35-6, Apr. 20, 2016. (Year: 2016).*
PCT International Search Report and Written Opinion dated Nov. 11, 2015.
The Scientific Assessment of Ozone Depletion, A report of the World Meteorological Association's Global Ozone Research and Monitoring Project, 2002, pp. 1.28-1.31, section 1.4.4.
2006 ASHRAE Refrigeration Handbook, Chapter 4, pp. 4.1-4.6.
Office Action in European Application No. 15766686.8, dated Nov. 7, 2018, 6 pages.

* cited by examiner

Primary Examiner — Douglas J McGinty

(57) ABSTRACT

A method for producing heating in a high temperature heat pump having a heat exchanger is provided. The method comprises extracting heat from a working fluid, thereby producing a cooled working fluid wherein said working fluid comprises (2E)-1,1,1,4,5,5,5-heptafluoro-4-(trifluoromethyl)pent-2-ene ("HFO-153-10mzzy"). Also, a high temperature heat pump apparatus is provided containing a working fluid comprising HFO-153-10mzzy. Also a composition is provided comprising (i) a working fluid consisting essentially of HFO-153-10mzzy; and (ii) a stabilizer to prevent degradation at temperatures of 55° C. or above, or (iii) a lubricant suitable for use at 55° C. or above, or both (ii) and (iii).

18 Claims, 3 Drawing Sheets

USE OF (2E)-1,1,1,4,5,5,5-HEPTAFLUORO-4-(TRIFLUOROMETHYL)PENT-2-ENE IN HIGH TEMPERATURE HEAT PUMPS

RELATED APPLICATIONS

This application represents a national filing under 35 U.S.C. 371 of international Application No. PCT/US2015/048234 filed Sep. 3, 2015, and claims priority to U.S. Provisional Patent Application 62/053,955, filed on Sep. 23, 2014.

BACKGROUND

Chlorofluorocarbons (CFCs) and hydrochlorofluorocarbons (HCFCs) have been employed in a wide range of applications, including their use in high temperature heat pumps. CFCs and HCFCs are suspected to contribute to the destruction of stratospheric ozone and to the increase in global warming. There is a continued need to seek alternative material compositions that do not contribute to the destruction of the ozone layer and also have a low global warming potential.

SUMMARY

Methods and systems for producing heat in numerous applications, and in particular, in high temperature heat pumps are provided.

This invention relates to compositions comprising (2E)-1,1,1,4,5,5,5-heptafluoro-4-(trifluoromethyl)pent-2-ene) (hereinafter "HFO-153-10mzzy"), as well as methods and systems using these compositions in high temperature heat pumps.

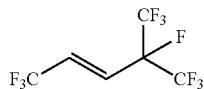

(2E)-1,1,1,4,5,5,5-heptafluoro-4-(trifluoromethyl)pent-2-ene

F13iE 153-10Mzzy

Embodiments of the present invention involve the compound HFO-153-10mzzy either alone or in combination with one or more other compounds as described in detail herein below.

In accordance with embodiments of this invention, a method for producing heating in a high temperature heat pump having a heat exchanger. The method comprises extracting heat from a working fluid, thereby producing a cooled working fluid wherein said working fluid comprises (2E)-1,1,1,4,5,5,5-heptafluoro-4-(trifluoromethyl)pent-2-ene.

Also in accordance with this invention, a method for producing heating in a high temperature heat pump is provided. The method comprises condensing a vapor working fluid comprising HFO-153-10mzzy, in a condenser, thereby producing a liquid working fluid.

Also in accordance with this invention, a method of raising the maximum feasible condenser operating temperature in a high temperature heat pump apparatus is provided. The method comprises charging the high temperature heat pump with a working fluid comprising HFO-153-10mzzy.

Also in accordance with this invention, a high temperature heat pump apparatus is provided. The apparatus contains a working fluid comprising HFO-153-10mzzy.

Also in accordance with this invention a composition is provided. The composition comprises: (i) a working fluid consisting essentially of HFO-153-10mzzy; and (ii) a stabilizer to prevent degradation at temperatures of 55° C. or above, or (iii) a lubricant suitable for use at 55° C. or above, or both (ii) and (iii).

DETAILED DESCRIPTION

Figure 1:
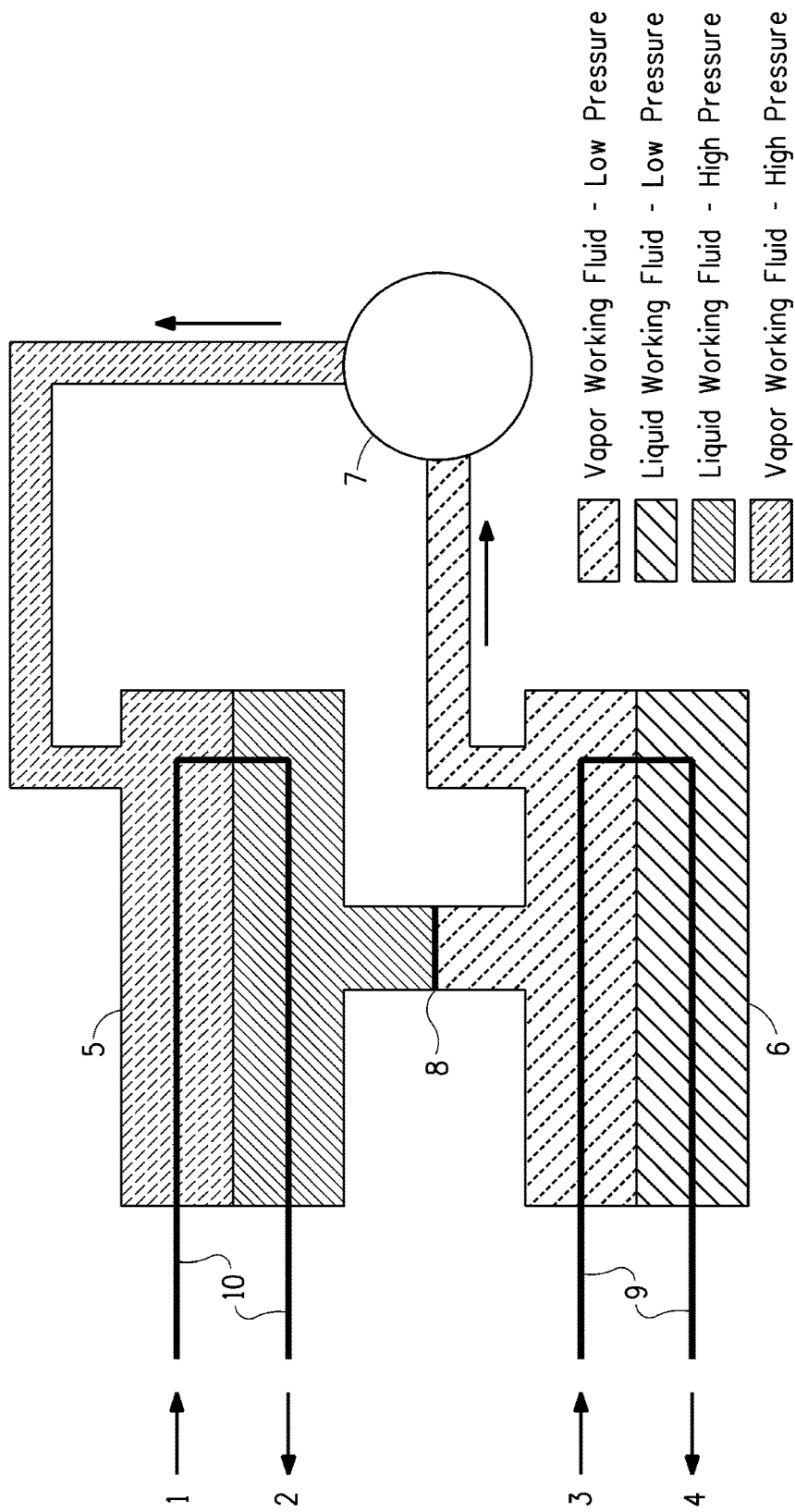
FIG. 1 is a schematic diagram of one embodiment of a flooded evaporator heat pump apparatus which utilizes a composition comprising HFO-153-10mzzy as working fluid.

Before addressing details of embodiments described below, some terms are defined or clarified.

Global warming potential (GWP) is an index for estimating relative global warming contribution due to atmospheric emission of a kilogram of a particular greenhouse gas compared to emission of a kilogram of carbon dioxide. GWP can be calculated for different time horizons showing the effect of atmospheric lifetime for a given gas. The GWP for the 100 year time horizon is commonly the value referenced.

Ozone depletion potential (ODP) is defined in "The Scientific Assessment of Ozone Depletion, 2002, A report of the World Meteorological Association's Global Ozone Research and Monitoring Project," section 1.4.4, pages 1.28 to 1.31 (see first paragraph of this section). ODP represents the extent of ozone depletion in the stratosphere expected from a compound on a mass-for-mass basis relative to fluorotrichloromethane (CFC-11).

Refrigeration capacity (sometimes referred to as cooling capacity) is a term to define the change in enthalpy of a refrigerant or working fluid in an evaporator per unit mass of refrigerant or working fluid circulated. Volumetric cooling capacity refers to the amount of heat removed by the refrigerant or working fluid in the evaporator per unit volume of refrigerant vapor exiting the evaporator. The refrigeration capacity is a measure of the ability of a refrigerant, working fluid or heat transfer composition to produce cooling. Therefore, the higher the volumetric cooling capacity of the working fluid, the greater the cooling rate that can be produced at the evaporator with the maximum volumetric flow rate achievable with a given compressor. Cooling rate refers to the heat removed by the refrigerant in the evaporator per unit time.

Similarly, volumetric heating capacity is a term to define the amount of heat supplied by the refrigerant or working fluid in the condenser per unit volume of refrigerant or working fluid vapor entering the compressor. The higher the volumetric heating capacity of the refrigerant or working fluid, the greater the heating rate that is produced at the condenser with the maximum volumetric flow rate achievable with a given compressor.

Coefficient of performance (COP) is the amount of heat removed in the evaporator divided by the energy required to operate the compressor. The higher the COP, the higher the energy efficiency. COP is directly related to the energy efficiency ratio (EER), that is, the efficiency rating for refrigeration or air conditioning equipment at a specific set of internal and external temperatures.

As used herein, a heat transfer medium comprises a composition used to carry heat from a body to be cooled to a chiller evaporator or from a chiller condenser to a cooling tower or other configuration where heat can be rejected to the ambient.

As used herein, a working fluid comprises a compound or mixture of compounds that function to transfer heat in a cycle wherein the working fluid undergoes a phase change from a liquid to a gas and back to a liquid in a repeating cycle.

Subcooling is the reduction of the temperature of a liquid below that liquid's saturation point for a given pressure. The saturation point is the temperature at which a vapor composition is completely condensed to a liquid (also referred to as the bubble point). But subcooling continues to cool the liquid to a lower temperature liquid at the given pressure. By cooling a liquid below the saturation temperature, the net refrigeration capacity can be increased. Subcooling thereby improves refrigeration capacity and energy efficiency of a system. Subcool amount is the amount of cooling below the saturation temperature (in degrees) or how far below its saturation temperature a liquid composition is cooled.

Superheat is a term that defines how far above the saturation vapor temperature of a vapor composition a vapor composition is heated. Saturation vapor temperature is the temperature at which, if a vapor composition is cooled, the first drop of liquid is formed, also referred to as the "dew point".

As used herein, the terms "comprises," "comprising," "includes," "including," "has," "having" or any other variation thereof, are intended to cover a non-exclusive inclusion. For example, a composition, process, method, article, or apparatus that comprises a list of elements is not necessarily limited to only those elements but may include other elements not expressly listed or inherent to such composition, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The transitional phrase "consisting of" excludes any element, step, or ingredient not specified. If in the claim such would close the claim to the inclusion of materials other than those recited except for impurities ordinarily associated therewith. When the phrase "consists of" appears in a clause of the body of a claim, rather than immediately following the preamble, it limits only the element set forth in that clause; other elements are not excluded from the claim as a whole.

The transitional phrase "consisting essentially of" is used to define a composition, method or apparatus that includes materials, steps, features, components, or elements, in addition to those literally disclosed provided that these additional included materials, steps, features, components, or elements do not materially affect the basic and novel characteristic(s) of the claimed invention. The term 'consisting essentially of' occupies a middle ground between "comprising" and 'consisting of'.

Where applicants have defined an invention or a portion thereof with an open-ended term such as "comprising," it should be readily understood that (unless otherwise stated) the description should be interpreted to also describe such an invention using the terms "consisting essentially of" or "consisting of."

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

(2E)-1,1,1,4,5,5,5-heptafluoro-4-(trifluoromethyl)pent-2-ene) ("HFO-153-10mzzy), can be prepared by dehydroiodination of 1,1,1,2,5,5,5-heptafluoro-2-(trifluoromethyl)-4-iodopentane as disclosed in U.S. Pat. No. 8,148,584, incorporated herein by reference.

High Temperature Heat Pump Methods

In accordance with this invention, a method for producing heating in a high temperature heat pump having a heat exchanger. The method comprises extracting heat from a working fluid, thereby producing a cooled working fluid wherein said working fluid comprises HFO-153-10mzzy.

In one embodiment, the heat exchanger is a supercritical working fluid cooler or just working fluid cooler. In another embodiment, the heat exchanger is a condenser.

In one embodiment is provided a method for producing heating in a high temperature heat pump comprising condensing a vapor working fluid comprising HFO-153-10mzzy, in a condenser, thereby producing a liquid working fluid. Of note are methods wherein a vapor working fluid consisting essentially of HFO-153-10mzzy is condensed.

Of particular utility in high temperature heat pumps are compositions comprising HFO-153-10mzzy. HFO-153-10mzzy meets the need for a non-flammable high temperature heat pump working fluid with reduced GWP.

Some high temperature heat pumps operated with HFO-153-10mzzy as the working fluid have vapor pressures below the threshold necessitating compliance with provisions of the ASME Boiler and Pressure Vessel Code. Such compositions are desirable for use in high temperature heat pumps. Of note are compositions where the working fluid consists essentially of from about 1 to about 100 weight percent HFO-153-10mzzy.

In one embodiment, the method for producing heating in a heat pump having a condenser or working fluid cooler, further comprises passing a heat transfer medium through the condenser or working fluid cooler, whereby cooling (and sometimes condensation) of the working fluid heats the heat transfer medium, and passing the heated heat transfer medium from the condenser or working fluid cooler to a body to be heated.

A body to be heated may be any space, object or fluid that may be heated. In one embodiment, a body to be heated may be a room, building, or the passenger compartment of an automobile. Alternatively, in another embodiment, a body to be heated may be a secondary loop fluid, heat transfer medium or heat transfer fluid.

In one embodiment, the heat transfer medium is water and the body to be heated is water. In another embodiment, the heat transfer medium is water and the body to be heated is air for space heating. In another embodiment, the heat transfer medium is an industrial heat transfer liquid and the body to be heated is a chemical process stream.

In another embodiment, the method to produce heating further comprises compressing the working fluid vapor in a dynamic (e.g. axial or centrifugal) compressor or in a positive displacement (e.g. reciprocating, screw or scroll) compressor.

In one embodiment, the method for producing heating in a heat pump having a condenser, further comprises passing a fluid to be heated through the condenser, thus heating the fluid. In one embodiment, the fluid is air, and the heated air from the condenser is passed to a space to be heated. In another embodiment, the fluid is a portion of a process stream, and the heated portion is returned to the process.

In certain embodiments, the heat transfer medium is selected from water or glycol. The glycol can be, for example, ethylene glycol or propylene glycol. Of particular note is an embodiment wherein the heat transfer medium is water and the body to be heated is air for space heating.

In another embodiment, the heat transfer medium is an industrial heat transfer liquid, and the body to be heated is a chemical process stream, which, as used herein, chemical process stream includes process lines and process equipment such as distillation columns. Of note are industrial heat transfer liquids including ionic liquids, various brines such as aqueous calcium chloride or sodium chloride, glycols such as propylene glycol or ethylene glycol, methanol, and other heat transfer media such as those listed in section 4 of the 2006 ASHRAE Handbook on Refrigeration.

In one embodiment, the method for producing heating comprises extracting heat in a flooded evaporator high temperature heat pump as described above with respect to FIG. 1, discussed in more detail herein below. In this method, the liquid working fluid is evaporated to form a working fluid vapor in the vicinity of a first heat transfer medium. The first heat transfer medium is a warm liquid, such as water, which is transported into the evaporator via a pipe from a low temperature heat source. The warm liquid is cooled and is returned to the low temperature heat source or is passed to a body to be cooled, such as a building. The working fluid vapor is then condensed in the vicinity of a second heat transfer medium, which is a chilled liquid which is brought in from the vicinity of a body to be heated (heat sink). The second heat transfer medium cools the working fluid such that it is condensed to form a liquid working fluid. In this method a flooded evaporator heat pump may also be used to heat domestic or service water or a process stream.

In another embodiment, the method for producing heating comprises producing heating in a direct expansion high temperature heat pump as described above with respect to FIG. 2, discussed in more detail herein below. In this method, working fluid liquid is passed through an evaporator and evaporates to produce a working fluid vapor. A first liquid heat transfer medium is cooled by the evaporating working fluid. The first liquid heat transfer medium is passed out of the evaporator to a low temperature heat source or a body to be cooled. The working fluid vapor is then condensed or cooled in the vicinity of a second heat transfer medium, which is a chilled liquid which is brought in from the vicinity of a body to be heated (heat sink). The second heat transfer medium cools the working fluid such that it is condensed to form a liquid working fluid. In this method, a direct expansion heat pump may also be used to heat domestic or service water or a process stream.

In one embodiment of the method for producing heating, the high temperature heat pump includes a compressor which is a centrifugal compressor.

In another embodiment of the invention a method is provided for raising the maximum feasible condenser operating temperature in a high temperature heat pump apparatus comprising charging the high temperature heat pump with a working fluid comprising HFO-153-10mzzy.

The critical temperature and pressure of HFO-153-10mzzy are 170.24° C. and 2.04 MPa (296.2 psia), respectively. The boiling point of HFO-153-10mzzy is 49° C. Compositions comprising HFO-153-10mzzy can have lower vapor pressures and higher critical temperatures than working fluids commonly used in high temperature heat pumps today, such as HFC-245fa. Use of a composition comprising HFO-153-10mzzy in a high temperature heat pump originally designed for a working fluid with a higher vapor pressure and a lower critical temperature than the said composition comprising HFO-153-10mzzy can allow operation of the high temperature heat pump at condenser temperatures higher than achievable with the working fluid for which the high temperature heat pump was originally designed. For example, the condenser temperature of a centrifugal heat pump with a maximum design working pressure of 2.18 MPa operating with HFC-245fa as the working fluid cannot exceed 126.2° C. Regardless of limitations on the maximum permissible working pressure, the maximum condenser temperature with HFC-245fa cannot exceed its critical temperature of about 154° C. However, the condenser temperature of a centrifugal heat pump with a maximum design working pressure of 2.18 MPa operating with HFO-153-10mzzy as the working fluid can reach temperatures approaching the critical temperature of HFO-15310mzzy of 170.24° C. without exceeding the maximum permissible design working pressure.

When HFO-153-10mzzy is used as the working fluid in a high temperature heat pump, the maximum feasible condenser operating temperature is about 160-170° C. In one embodiment of the method to raise the maximum feasible condenser operating temperature, when a composition comprising HFO-153-10mzzy, is used as the heat pump working fluid, the maximum feasible condenser operating temperature is raised to a temperature equal to or greater than about 165° C.

It is feasible that heating temperatures as high as 200-250° C. are achievable with a high temperature heat pump utilizing HFO-153-10mzzy. However at heating temperatures above about 165° C., some modification of equipment or materials, may be necessary to accommodate the higher pressures associated with these higher temperatures and to extract heat from the working fluid at temperatures above its critical temperature without condensation (i.e. in a transcritical mode of operation).

In accordance with this invention it is possible to replace a high temperature heat pump fluid (for example, HFC-245fa) in a system originally designed for said high temperature heat pump fluid with a working fluid comprising HFO-153-10mzzy in order to raise the condenser operating temperature.

A composition comprising HFO-153-10mzzy enables the design and operation of dynamic (e.g. centrifugal) or positive displacement (e.g. screw or scroll) heat pumps for upgrading heat available at low temperatures to meet demands for heating at higher temperatures. The available low temperature heat is supplied to the evaporator and the high temperature heat is extracted at the condenser or working fluid cooler (in a supercritical or transcritical mode). For example, waste heat can be available to be supplied to the evaporator of a heat pump operating at 25° C. at a location (e.g. a hospital) where heat from the condenser, operating at 85° C., can be used to heat water (e.g. for hydronic space heating or other service).

In some cases heat may be available from various other sources (e.g. waste heat from process streams, geothermal heat or solar heat) at temperatures higher than suggested above, while heating at even higher temperatures may be required. For example, waste heat may be available at 100° C. while heating at 130° C. may be required for an industrial application. The lower temperature heat can be supplied to the evaporator of a dynamic (e.g. centrifugal) or positive displacement heat pump in the method or system of this invention to be uplifted to the desired temperature of 130° C. and be delivered at the condenser. In another example, waste heat can be available to be supplied to the evaporator of a heat pump operating with HFO-153-10mzzy as the working fluid at 130° C. at a location (e.g. an industrial operation) where heat from the condenser, operating at 165° C., can be used to heat a process stream.

High Temperature Heat Pump Apparatus

In one embodiment of the present invention is provided a heat pump apparatus containing a working fluid comprising HFO-153-10mzzy. Of note are embodiments wherein the working fluid consists essentially of HFO-153-10mzzy.

A heat pump is a type of apparatus for producing heating and/or cooling. A heat pump includes an evaporator, a compressor, a condenser or working fluid cooler, and an expansion device. A working fluid circulates through these components in a repeating cycle. Heating is produced at the condenser or working fluid cooler where energy (in the form of heat) is extracted from the vapor (or supercritical fluid) working fluid as it is condensed (or cooled) to form liquid working fluid. Cooling is produced at the evaporator where energy is absorbed to evaporate the working fluid to form vapor working fluid.

In one embodiment, the heat pump apparatus comprises an evaporator, a compressor, a condenser (or working fluid cooler) and a pressure reduction device, all of which are in fluid communication in the order listed and through which a working fluid flows from one component to the next in a repeating cycle.

In one embodiment the heat pump apparatus comprises (a) an evaporator through which a working fluid flows and is evaporated; (b) a compressor in fluid communication with the evaporator that compresses the evaporated working fluid to a higher pressure; (c) a condenser in fluid communication with the compressor through which the high pressure working fluid vapor flows and is condensed; and (d) a pressure reduction device in fluid communication with the condenser wherein the pressure of the condensed working fluid is reduced and said pressure reduction device further being in fluid communication with the evaporator such that the working fluid may repeat flow through components (a), (b), (c) and (d) in a repeating cycle; wherein the working fluid comprises HFO-153-10mzzy.

Figure 2:
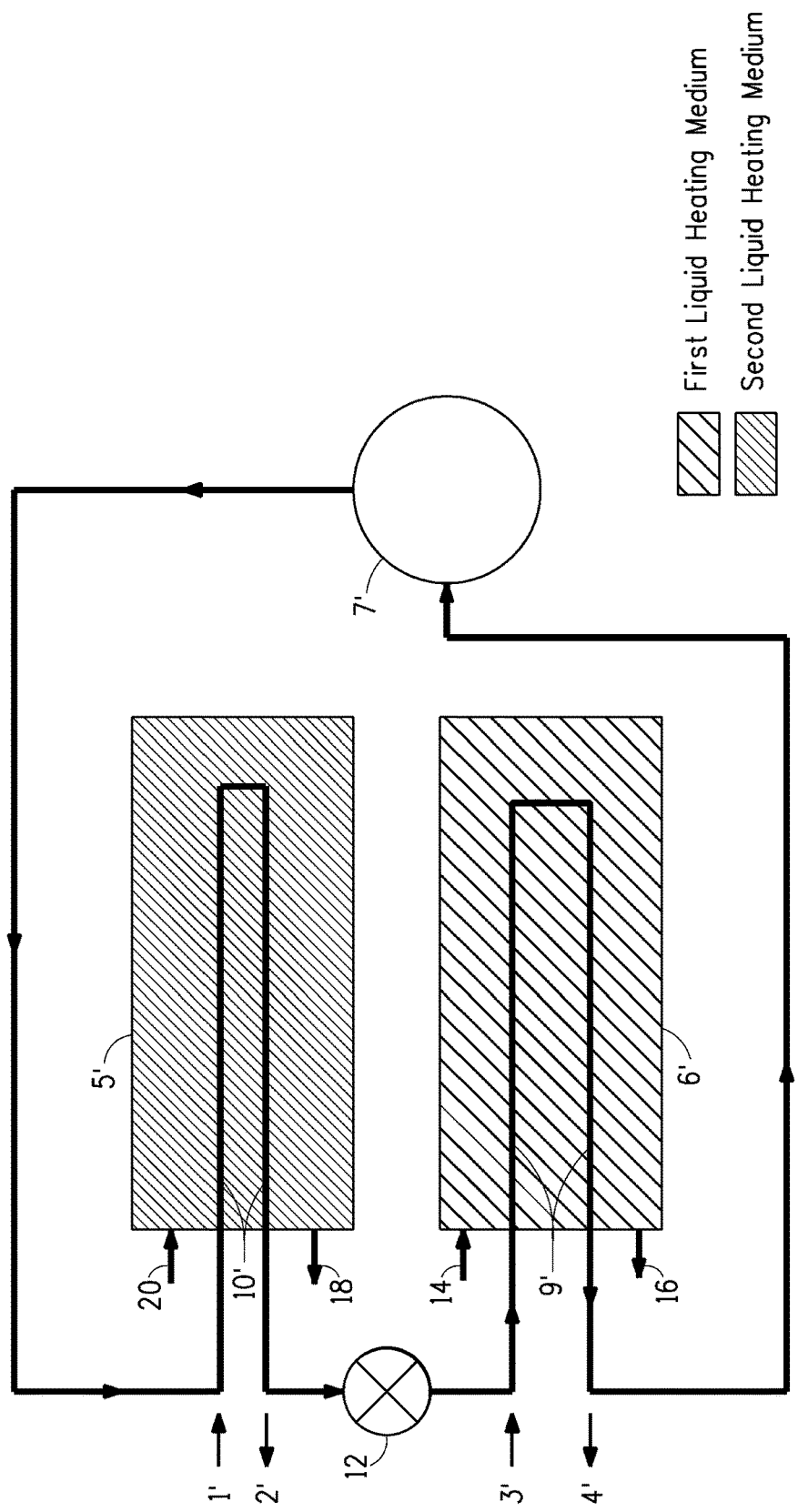
FIG. 2 is a schematic diagram of one embodiment of a direct expansion heat pump apparatus which utilizes a composition comprising HFO-153-10mzzy as working fluid.

Heat pumps for use in this invention include flooded evaporators, one embodiment of which is shown in FIG. 1, and direct expansion evaporators, one embodiment of which is shown in FIG. 2.

Heat pumps may utilize positive displacement compressors or dynamic compressors (e.g. centrifugal compressors or axial compressors). Positive displacement compressors include reciprocating, screw, or scroll compressors. Of note are heat pumps that use screw compressors. Also of note are heat pumps that use centrifugal compressors.

Residential heat pumps are used to produce heated air to warm a residence or home (including single family or multi-unit attached homes) and produce maximum condenser operating temperatures from about 30° C. to about 50° C.

Of note are high temperature heat pumps that may be used to heat air, water, another heat transfer medium or some portion of an industrial process, such as a piece of equipment, storage area or process stream. These high temperature heat pumps can produce maximum condenser operating temperatures greater than about 55° C. The maximum condenser operating temperature that can be achieved in a high temperature heat pump depends on the working fluid used. This maximum condenser operating temperature is limited by the normal boiling characteristics of the working fluid and also by the pressure to which the heat pump's compressor can raise the vapor working fluid pressure. This maximum pressure is also related to the working fluid used in the heat pump.

Of particular value are high temperature heat pumps that operate at condenser temperatures of at least about 75° C. Also of note are high temperature heat pumps that operate at condenser temperatures of at least about 100° C. Also of note high temperature heat pumps that operate at condenser temperatures of at least about 125° C. Compositions comprising HFO-153-10mzzy enable the design and operation of centrifugal heat pumps, operated at condenser temperatures higher than those accessible with many currently available working fluids. Of note are embodiments using working fluids comprising HFO-153-10mzzy operated at condenser temperatures up to about 160 to 169° C.

Also of note are heat pumps that are used to produce heating and cooling simultaneously. For instance, a single heat pump unit may produce hot water for domestic use and may also produce cooling for comfort air conditioning in the summer.

Heat pumps, including both flooded evaporator and direct expansion, may be coupled with an air handling and distribution system to provide comfort air conditioning (cooling and dehumidifying the air) and/or heating to residence (single family or attached homes) and large commercial buildings, including hotels, office buildings, hospitals, schools, universities, and the like. In another embodiment, heat pumps may be used to heat water.

To illustrate how heat pumps operate, reference is made to the Figures. One embodiment of a flooded evaporator heat pump is shown in FIG. 1. In this heat pump a first heat transfer medium, which is a warm liquid, which comprises water, and, in some embodiments, additives, or other heat transfer medium such as a glycol (e.g., ethylene glycol or propylene glycol), enters the heat pump carrying heat from a low temperature source (not shown), such as a building air handling system or warmed-up water from condensers of a chiller plant flowing to a cooling tower, shown entering the heat pump at arrow 3, through a tube bundle or coil 9, in an evaporator 6, which has an inlet and an outlet. The warm first heat transfer medium is delivered to evaporator 6, where it is cooled by liquid working fluid, which is shown in the lower portion of evaporator 6. The liquid working fluid evaporates at a lower temperature than the warm first heat transfer medium which flows through tube bundle or coil 9. The cooled first heat transfer medium re-circulates back to the low temperature heat source as shown by arrow 4, via a return portion of tube bundle or coil 9. The liquid working fluid, shown in the lower portion of evaporator 6, vaporizes and is drawn into compressor 7, which increases the pressure and temperature of the working fluid vapor. Compressor 7 compresses this vapor so that it may be condensed in condenser 5 at a higher pressure and temperature than the pressure and temperature of the working fluid vapor when it exits evaporator 6. A second heat transfer medium enters the condenser via a tube bundle or coil 10 in condenser 5 from a location where high temperature heat is provided ("heat sink") such as a domestic or service water heater or a hydronic heating system at arrow 1. The second heat transfer medium is warmed in the process and returned via a return loop of tube bundle or coil 10 and arrow 2 to the heat sink. This second heat transfer medium cools the working fluid vapor in condenser 5 and causes the vapor to condense to liquid working fluid, so that there is liquid working fluid in the lower portion of condenser 5. Condensed liquid working fluid in condenser 5 flows back to evaporator 6 through expansion device 8, which may be an orifice, capillary tube or expansion valve. Expansion device 8 reduces the pressure of the liquid working fluid, and converts the liquid working fluid partially to vapor, that is to say that the liquid working fluid flashes as pressure drops between condenser 5 and evaporator 6. Flashing cools the working fluid, i.e., both the liquid working fluid and the working fluid vapor to the saturated temperature at evaporator pressure, so that both liquid working fluid and working fluid vapor are present in evaporator 6.

In some embodiments the working fluid vapor is compressed to a supercritical state and condenser 5 is replaced by a gas cooler where the working fluid vapor is cooled to a liquid state without condensation.

In some embodiments the first heat transfer medium used in the apparatus depicted in FIG. 1 is chilled water returning from a building where air conditioning is provided or from some other body to be cooled. Heat is extracted from the returning chilled water at evaporator 6 and the cooled chilled water is supplied back to the building or other body to be cooled. In this embodiment the apparatus depicted in FIG. 1 functions to simultaneously cool the first heat transfer medium that provides cooling to a body to be cooled (e.g. building air) and heat the second heat transfer medium that provides heating to a body to be heated (e.g. domestic or service water or process stream).

It is understood that the apparatus depicted in FIG. 1 can extract heat at evaporator 6 from a wide variety of heat sources including solar, geothermal and waste heat and supply heat from condenser 5 to a wide range of heat sinks.

It should be noted that for a single component working fluid composition, the composition of the vapor working fluid in the evaporator and condenser is the same as the composition of the liquid working fluid in the evaporator and condenser. In this case, evaporation will occur at a constant temperature. However, if a working fluid blend (or mixture) is used, as in the present invention, the liquid working fluid and the working fluid vapor in the evaporator (or in the condenser) may have different compositions. This may lead to inefficient systems and difficulties in servicing the equipment, thus a single component working fluid is more desirable. An azeotrope or azeotrope-like composition will function essentially as a single component working fluid in a heat pump, such that the liquid composition and the vapor composition are essentially the same reducing any inefficiency that might arise from the use of a non-azeotropic or non-azeotrope-like composition.

One embodiment of a direct expansion heat pump is illustrated in FIG. 2. In the heat pump as illustrated in FIG. 2, first liquid heat transfer medium, which is a warm liquid, such as warm water, enters evaporator 6' at inlet 14. Mostly liquid working fluid (with a small amount of working fluid vapor) enters coil 9' in the evaporator at arrow 3' and evaporates. As a result, first liquid heating medium is cooled in evaporator 6', and a cooled first liquid heating medium exits evaporator 6' at outlet 16, and is sent to low temperature heat source (e.g. warm water flowing to a cooling tower). The working fluid vapor exits evaporator 6' at arrow 4' and is sent to compressor 7', where it is compressed and exits as high temperature, high pressure working fluid vapor. This working fluid vapor enters condenser 5' through condenser coil 10' at 1'. The working fluid vapor is cooled by a second liquid heating medium, such as water, in condenser 5' and becomes a liquid. The second liquid heating medium enters condenser 5' through condenser heat transfer medium inlet 20. The second liquid heating medium extracts heat from the condensing working fluid vapor, which becomes liquid working fluid, and this warms the second liquid heating medium in condenser 5'. The second liquid heating medium exits from condenser 5' through condenser heat transfer medium outlet 18. The condensed working fluid exits condenser 5' through lower coil 10' and flows through expansion device 12, which may be an orifice, capillary tube or expansion valve. Expansion device 12 reduces the pressure of the liquid working fluid. A small amount of vapor, produced as a result of the expansion, enters evaporator 6' with liquid working fluid through coil 9' and the cycle repeats.

In some embodiments the working fluid vapor is compressed to a supercritical state and condenser 5' is replaced by a gas cooler where the working fluid vapor is cooled to a liquid state without condensation.

In some embodiments the first heat transfer medium used in the apparatus depicted in FIG. 2 is chilled water returning from a building where air conditioning is provided or from some other body to be cooled. Heat is extracted from the returning chilled water at the evaporator 6' and the cooled chilled water is supplied back to the building or other body to be cooled. In this embodiment the apparatus depicted in FIG. 2 functions to simultaneously cool the first heat transfer medium that provides cooling to a body to be cooled (e.g. building air) and heat the second heat transfer medium that provides heating to a body to be heated (e.g. domestic or service water or process stream).

It is understood that the apparatus depicted in FIG. 2 can extract heat at the evaporator 6' from a wide variety of heat sources including solar, geothermal and waste heat and supply heat from the condenser 5' to a wide range of heat sinks.

Compressors useful in the present invention include dynamic compressors. Of note as examples of dynamic compressors are centrifugal compressors. A centrifugal compressor uses rotating elements to accelerate the working fluid radially, and typically includes an impeller and diffuser housed in a casing. Centrifugal compressors usually take working fluid in at an impeller eye, or central inlet of a circulating impeller, and accelerate it radially outward through passages. Some static pressure rise occurs in the impeller, but most of the pressure rise occurs in the diffuser section of the casing, where velocity is converted to static pressure. Each impeller-diffuser set is a stage of the compressor. Centrifugal compressors are built with from 1 to 12 or more stages, depending on the final pressure desired and the volume of refrigerant to be handled.

The pressure ratio, or compression ratio, of a compressor is the ratio of absolute discharge pressure to the absolute inlet pressure. Pressure delivered by a centrifugal compressor is practically constant over a relatively wide range of capacities. The pressure a centrifugal compressor can develop depends on the tip speed of the impeller. Tip speed is the speed of the impeller measured at its tip and is related to the diameter of the impeller and its revolutions per minute. The tip speed required in a specific application depends on the compressor work that is required to elevate the thermodynamic state of the working fluid from evaporator to condenser conditions. Volumetric flow capacity of a centrifugal compressor is determined by the size of the passages through the impeller. This makes the size of the compressor more dependent on the pressure required than the volumetric flow capacity required.

Also of note as examples of dynamic compressors are axial compressors. A compressor in which the fluid enters and leaves in the axial direction is called an axial flow compressor. Axial compressors are rotating, airfoil- or blade-based compressors in which a working fluid principally flows parallel to the axis of rotation. This is in contrast with other rotating compressors such as centrifugal or mixed-flow compressors in which a working fluid may enter axially but will have a significant radial component on exit. Axial flow compressors produce a continuous flow of compressed gas, and have the benefits of high efficiencies and large mass flow capacity, particularly in relation to their cross-section. They do, however, require several rows of airfoils to achieve large pressure rises making them complex and expensive relative to other designs.

Compressors useful in the present invention also include positive displacement compressors. Positive displacement compressors draw vapor into a chamber, and the chamber decreases in volume to compress the vapor. After being compressed, the vapor is forced from the chamber by further decreasing the volume of the chamber to zero or nearly zero.

Of note as examples of positive displacement compressors are reciprocating compressors. Reciprocating compressors use pistons driven by a crankshaft. They can be either stationary or portable, can be single or multi-staged, and can be driven by electric motors or internal combustion engines. Small reciprocating compressors from 5 to 30 hp are seen in automotive applications and are typically for intermittent duty. Larger reciprocating compressors up to 100 hp are found in large industrial applications. Discharge pressures can range from low pressure to very high pressure (above 5000 psi or 35 MPa).

Also of note as examples of positive displacement compressors are screw compressors. Screw compressors use two meshed rotating positive-displacement helical screws to force the gas into a smaller space. Screw compressors are usually for continuous operation in commercial and industrial application and may be either stationary or portable. Their application can be from 5 hp (3.7 kW) to over 500 hp (375 kW) and from low pressure to very high pressure (above 1200 psi or 8.3 MPa).

Also of note as examples of positive displacement compressors are scroll compressors. Scroll compressors are similar to screw compressors and include two interleaved spiral-shaped scrolls to compress the gas. The output is more pulsed than that of a rotary screw compressor.

In one embodiment, the high temperature heat pump apparatus of the present invention has at least two heating stages arranged as a cascade heating system, wherein each stage is in thermal communication with the next stage and wherein each stage circulates a working fluid therethrough, wherein heat is transferred to the final stage from the immediately preceding stage and wherein the heating fluid of the final stage comprises HFO-153-10mzzy.

In some embodiments, the high temperature heat pump apparatus of the present invention has at least two heating stages arranged as a cascade heating system, each stage being in thermal communication and the next stage circulating a working fluid therethrough, wherein said apparatus comprises (a) a first expansion device for reducing the pressure and temperature of a first working fluid liquid; (b) an evaporator in fluid communication with the first expansion device having an inlet and an outlet. The first working fluid liquid from the first expansion device enters the evaporator through the evaporator inlet and is evaporated in the evaporator to form a first working fluid vapor, and circulates to the evaporator outlet. The apparatus further comprises (c) a first compressor in fluid communication with the evaporator having an inlet and an outlet. The first working fluid vapor from the evaporator outlet circulates to the inlet of the first compressor and is compressed, thereby increasing the pressure and the temperature of the first working fluid vapor, and the compressed first refrigerant vapor circulates to the outlet of the first compressor. The apparatus further comprises (d) a cascade heat exchanger system in fluid communication with the first compressor outlet having: (i) a first inlet and a first outlet, and (ii) a second inlet and a second outlet in thermal communication with the first inlet and outlet. The first working fluid vapor from the first compressor circulates from the first inlet to the first outlet and is condensed in the heat exchanger system to form a first working fluid liquid, thereby rejecting heat. A second working fluid liquid circulates from the second inlet to the second outlet and absorbs the heat rejected by the first working fluid and forms a second working fluid vapor. The apparatus further comprises (e) a second compressor in fluid communication with the second outlet of the cascade heat exchanger system, said second compressor having an inlet and an outlet. The second working fluid vapor from the cascade heat exchanger system second outlet is drawn into the compressor and is compressed, thereby increasing the pressure and temperature of the second working fluid vapor. The apparatus further comprises (f) a condenser in fluid communication with the second compressor having an inlet and an outlet for circulating the second working fluid vapor therethrough and for condensing the second working fluid vapor from the compressor to form a second working fluid liquid, thereby producing heat. The second working fluid liquid exits the condenser through the outlet. The apparatus further comprises (g) a second expansion device in fluid communication with the condenser for reducing the pressure and temperature of the second working fluid liquid exiting the condenser and entering the second inlet of the cascade heat exchanger system. The second working fluid comprises HFO-153-10mzzy.

In one embodiment, the high temperature heat pump apparatus may comprise more than one heating circuit (or loop). The performance (coefficient of performance for heating and volumetric heating capacity) of high temperature heat pumps operated with HFO-153-10mzzy as the working fluid is drastically improved when the evaporator is operated at temperatures approaching the condenser temperature required by the application. When the heat supplied to the evaporator is only available at low temperatures, thus requiring high temperature lifts leading to poor performance, a dual fluid/dual circuit cascade cycle configuration is advantageous. The low stage or low temperature circuit of the cascade cycle is operated with a fluid of lower boiling point than HFO-153-10mzzy and preferably with a low GWP, including HFO-1234yf (2,3,3,3-tetrafluoropropene), HFO-1234ze-E (E-1,3,3,3-tetrafluoropropene), HFO-1234ye (1,2,3,3-tetrafluoropropene), HFO-1243zf (3,3,3-trifluoropropene), HFC-32 (difluoromethane), HFC-125 (pentafluoroethane), HFC-134a (1,1,1,2-tetrafluoroethane), HFC-134 (1,1,2,2-tetrafluoroethane), HFC-143a (1,1,1-trifluoroethane), HFC-152a (1,1-difluoroethane), HFC-227ea (1,1,1,2,3,3,3-heptafluoropropane) and their blends such as HFO-1234yf/HFC-32, HFO-1234yf/HFC-32/HFC-125, HFO-1234yf/HFC-134a, HFO-1234yf/HFC-134a/HFC-32, HFO-1234yf/HFC-134, HFO-1234yf/HFC-134a/HFC-134, HFO-1234yf/HFC-32/HFC-125/HFC-134a, HFO-1234ze-E/HFC-134a, HFO-1234ze-E/HFC-134, HFO-1234ze-E/HFC-134a/HFC-134, HFO-1234ze-E/HFC-227ea, HFO-1234ze-E/HFC-134/HFC-227ea, HFO-1234ze-E/HFC-134/HFC-134a/HFC-227ea, HFO-1234yf/HFO-1234ze-E/HFC-134/HFC-134a/HFC-227ea, etc. The evaporator of the low temperature circuit (or low temperature loop) of the cascade cycle receives the available low temperature heat, lifts the heat to a temperature intermediate between the temperature of the available low temperature heat and the temperature of the required heating duty and transfers the heat to the high stage or high temperature circuit (or high temperature loop) of the cascade system at a cascade heat exchanger. Then the high temperature circuit, operated with HFO-153-10mzzy, further lifts the heat received at the cascade heat exchanger to the required condenser temperature to meet the intended heating duty. The cascade concept may be extended to configurations with three or more circuits lifting heat over wider temperature ranges and using different fluids over different temperature sub-ranges to optimize performance.

In one embodiment of the high temperature heat pump apparatus having more than one stage, the first working fluid comprises at least one fluoroolefin selected from the group consisting of HFO-1234yf, E-HFO-1234ze, HFO-1234ye (E- or Z-isomer), and HFC-1243zf.

In another embodiment of the high temperature heat pump apparatus having more than one stage, the first working fluid comprises at least one fluoroalkane selected from the group consisting of HFC-32, HFC-125, HFC-134a, HFC-134, HFC-143a, HFC-152a and HFC-227ea.

In another embodiment of the high temperature heat pump apparatus having more than one stage, the working fluid of the stage preceding the final stage comprises at least one fluoroolefin selected from the group consisting of HFO-1234yf, E-HFO-1234ze, HFO-1234ye (E- or Z-isomer), and HFC-1243zf.

In another embodiment of the high temperature heat pump apparatus having more than one stage, wherein the working fluid of the stage preceding the final stage comprises at least one fluoroalkane selected from the group consisting of HFC-32, HFC-125, HFC-134a, HFC-134, HFC-143a, HFC-152a and HFC-227ea.

Figure 3:
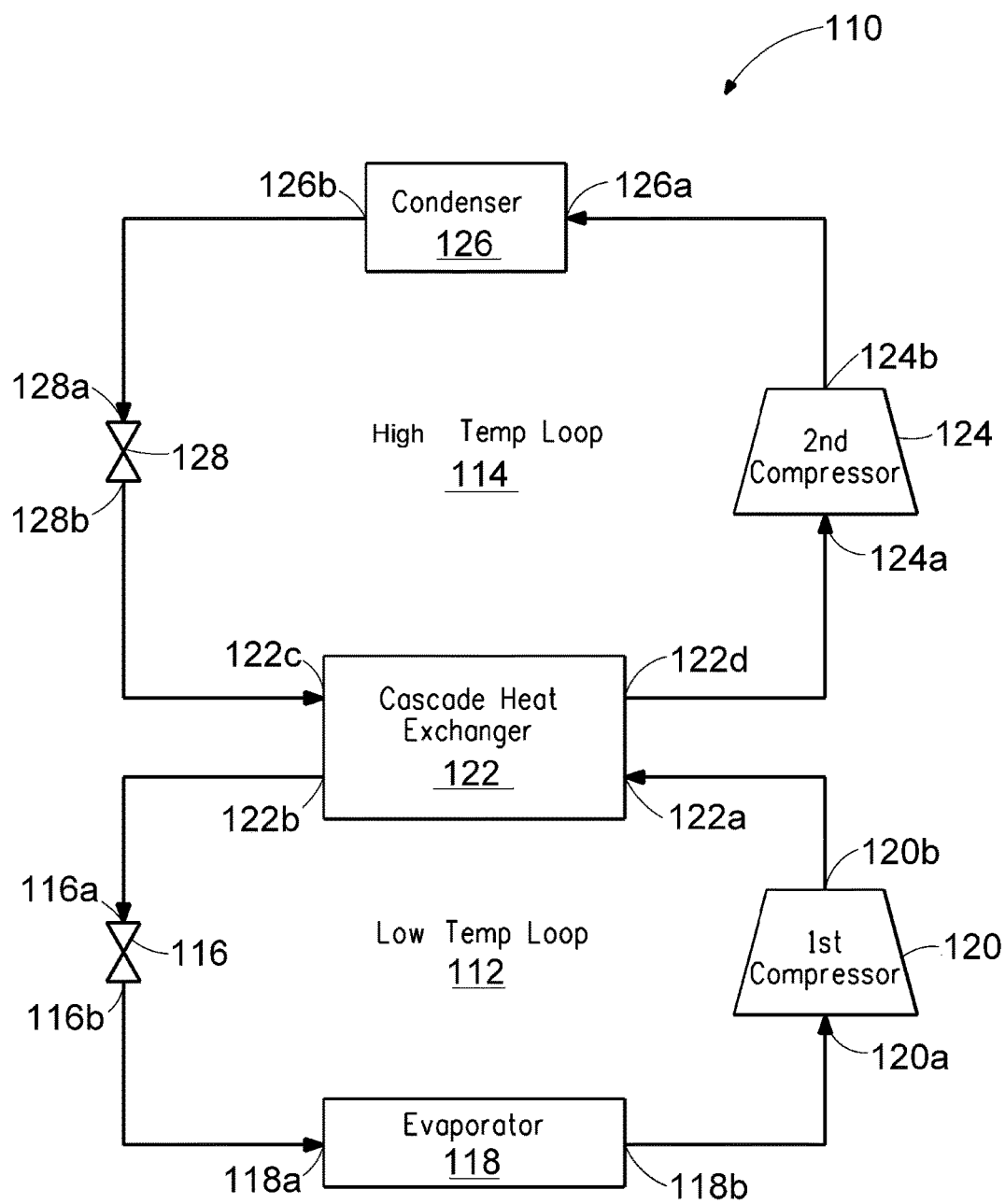
FIG. 3 is a schematic diagram of a cascade heat pump system which uses a composition comprising HFO-153-10mzzy as working fluid.

In accordance with the present invention, there is provided a cascade heat pump system having at least two heating loops for circulating a working fluid through each loop. One embodiment of such a cascade system is shown generally at 110 in FIG. 3. Cascade heat pump system 110 of the present invention has at least two heating loops, including a first, or lower loop 112, which is a low temperature loop, and a second, or upper loop 114, which is a high temperature loop 114. Each circulates a working fluid therethrough.

Cascade heat pump system 110 includes first expansion device 116. First expansion device 116 has an inlet 116a and an outlet 116b. First expansion device 116 reduces the pressure and temperature of a first working fluid liquid which circulates through the first or low temperature loop 112.

Cascade heat pump system 110 also includes evaporator 118. Evaporator 118 has an inlet 118a and an outlet 118b. The first working fluid liquid from first expansion device 116 enters evaporator 118 through evaporator inlet 118a and is evaporated in evaporator 118 to form a first working fluid vapor. The first working fluid vapor then circulates to evaporator outlet 118b.

Cascade heat pump system 110 also includes first compressor 120. First compressor 120 has an inlet 120a and an outlet 120b. The first working fluid vapor from evaporator 118 circulates to inlet 120a of first compressor 120 and is compressed, thereby increasing the pressure and the temperature of the first working fluid vapor. The compressed first working fluid vapor then circulates to the outlet 120b of the first compressor 120.

Cascade heat pump system 110 also includes cascade heat exchanger system 122. Cascade heat exchanger 122 has a first inlet 122a and a first outlet 122b. The first working fluid vapor from first compressor 120 enters first inlet 122a of heat exchanger 122 and is condensed in heat exchanger 122 to form a first working fluid liquid, thereby rejecting heat. The first working fluid liquid then circulates to first outlet 122b of heat exchanger 122. Heat exchanger 122 also includes a second inlet 122c and a second outlet 122d. A second working fluid liquid circulates from second inlet 122c to second outlet 122d of heat exchanger 122 and is evaporated to form a second working fluid vapor, thereby absorbing the heat rejected by the first working fluid (as it is condensed). The second working fluid vapor then circulates to second outlet 122d of heat exchanger 122. Thus, in the embodiment of FIG. 3, the heat rejected by the first working fluid is directly absorbed by the second working fluid.

Cascade heat pump system 110 also includes second compressor 124. Second compressor 124 has an inlet 124a and an outlet 124b. The second working fluid vapor from cascade heat exchanger 122 is drawn into compressor 124 through inlet 124a and is compressed, thereby increasing the pressure and temperature of the second working fluid vapor. The second working fluid vapor then circulates to outlet 124b of second compressor 124.

Cascade heat pump system 110 also includes condenser 126 having an inlet 126a and an outlet 126b. The second working fluid from second compressor 124 circulates from inlet 126a and is condensed in condenser 126 to form a second working fluid liquid, thus producing heat. The second working fluid liquid exits condenser 126 through outlet 126b.

Cascade heat pump system 110 also includes second expansion device 128 having an inlet 128a and an outlet 128b. The second working fluid liquid passes through second expansion device 128, which reduces the pressure and temperature of the second working fluid liquid exiting condenser 126. This liquid may be partially vaporized during this expansion. The reduced pressure and temperature second working fluid liquid circulates to second inlet 122c of cascade heat exchanger system 122 from expansion device 128.

Moreover, in the event that HFO-153-10mzzy is stable at temperatures higher than the critical temperature, then these working fluids enable design of heat pumps operated according to a supercritical and/or transcritical cycle in which heat is rejected by the working fluid in a supercritical state and made available for use over a range of temperatures (including temperatures higher that the critical temperature of HFO-153-10mzzy). The supercritical fluid is cooled to a liquid state without passing through an isothermal condensation transition.

For high temperature condenser operation (associated with high temperature lifts and high compressor discharge temperatures) formulations of working fluid (e.g. HFO-153-10mzzy) and lubricants with high thermal stability (possibly in combination with oil cooling or other mitigation approaches) will be advantageous.

For high temperature condenser operation (associated with high temperature lifts and high compressor discharge temperatures) use of magnetic centrifugal compressors (e.g. Danfoss-Turbocor type) that do not require the use of lubricants will be advantageous.

For high temperature condenser operation (associated with high temperature lifts and high compressor discharge temperatures) use of compressor materials (e.g. shaft seals, etc) with high thermal stability may also be required.

The composition comprising HFO-153-10mzzy may be used in a high temperature heat pump apparatus in combination with molecular sieves to aid in removal of moisture. Desiccants may comprise activated alumina, silica gel, or zeolite-based molecular sieves. In certain embodiments, the preferred molecular sieves have a pore size of approximately 3 Angstroms, 4 Angstroms, or 5 Angstroms. Representative molecular sieves include MOLSIV XH-7, XH-6, XH-9 and XH-11 (UOP LLC, Des Plaines, Ill.).

High Temperature Heat Pump Compositions

A composition is provided for use in high temperature heat pumps. The composition comprises: (i) a working fluid consisting essentially of HFO-153-10mzzy and (ii) a stabilizer to prevent degradation at temperatures of 55° C. or above, or (iii) a lubricant suitable for use at 55° C. or above, or both (ii) and (iii). Of note are compositions wherein the working fluid component consists essentially of HFO-153-10mzzy.

High temperature heat pumps operated with HFO-153-10mzzy can have vapor pressures below the threshold (15 psig) necessitating compliance with provisions of the ASME Boiler and Pressure Vessel Code. Such compositions are desirable for use in high temperature heat pumps.

Further, in another embodiment, low GWP compositions are desirable. Of note are compositions comprising at least 1-100 weight of HFO-153-10mzzy, which have GWP values lower than 1500, preferably lower than 1000, more preferably lower than 750, more preferably lower than 500, more preferably lower than 150 and even more preferably lower than 10. The compositions of the present invention can be prepared by any convenient method including mixing or combining the desired amounts. In one embodiment of this invention, a composition can be prepared by weighing the desired component amounts and thereafter combining them in an appropriate vessel.

The composition comprising HFO-153-10mzzy may also comprise and/or be used in combination with at least one lubricant selected from the group consisting of polyalkylene glycols, polyol esters, polyvinylethers, mineral oils, alkylbenzenes, synthetic paraffins, synthetic naphthenes, and poly (alpha)olefins.

Useful lubricants include those suitable for use with high temperature heat pump apparatus. Among these lubricants are those conventionally used in vapor compression refrigeration apparatus utilizing chlorofluorocarbon refrigerants. In one embodiment, lubricants comprise those lubricants commonly known as "mineral oils" in the field of compression refrigeration lubrication. Mineral oils comprise paraffins (i.e., straight-chain and branched-carbon-chain, saturated hydrocarbons), naphthenes (i.e. cyclic paraffins) and aromatics (i.e. unsaturated, cyclic hydrocarbons containing one or more rings characterized by alternating double bonds). In one embodiment, lubricants comprise those commonly known as "synthetic oils" in the field of compression refrigeration lubrication. Synthetic oils comprise alkylaryls (i.e. linear and branched alkyl alkylbenzenes), synthetic paraffins and naphthenes, and poly(alphaolefins). Representative conventional lubricants are the commercially available BVM 100 N (paraffinic mineral oil sold by BVA Oils), naphthenic mineral oil commercially available from Crompton Co. under the trademarks Suniso® 3GS and Suniso® 5GS, naphthenic mineral oil commercially available from Pennzoil under the trademark Sontex® 372LT, naphthenic mineral oil commercially available from Calumet Lubricants under the trademark Calumet® RO-30, linear alkylbenzenes commercially available from Shrieve Chemicals under the trademarks Zerol® 75, Zerol® 150 and Zerol® 500, and HAB 22 (branched alkylbenzene sold by Nippon Oil).

Useful lubricants may also include those which have been designed for use with hydrofluorocarbon refrigerants and are miscible with refrigerants of the present invention under compression refrigeration and air-conditioning apparatus' operating conditions. Such lubricants include, but are not limited to, polyol esters (POEs) such as Castrol® 100 (Castrol, United Kingdom), polyalkylene glycols (PAGs) such as RL-488A from Dow (Dow Chemical, Midland, Mich.), polyvinyl ethers (PVEs), and polycarbonates (PCs).

Lubricants are selected by considering a given compressor's requirements and the environment to which the lubricant will be exposed.

Of note are high temperature lubricants with stability at high temperatures. The highest temperature the heat pump will achieve will determine which lubricants are required. In one embodiment, the lubricant must be stable at temperatures of at least 55° C. In another embodiment, the lubricant must be stable at temperatures of at least 75° C. In another embodiment, the lubricant must be stable at temperatures of at least 100° C. In another embodiment, the lubricant must be stable at temperatures of at least 139° C. In another embodiment, the lubricant must be stable at temperatures of at least 145° C. In another embodiment, the lubricant must be stable at temperatures of at least 155° C. In another embodiment, the lubricant must be stable at temperatures of at least 165° C. In another embodiment the lubricant must be stable at temperatures of at least 170° C. In another embodiment the lubricant must be stable at temperatures of at least 200° C. In another embodiment the lubricant must be stable at temperatures of at least 250° C.

Of particular note are poly alpha olefin (POA) lubricants with stability up to about 200° C. and polyol ester (POE) lubricants with stability at temperatures up to about 200 to 220° C. Also of particular note are perfluoropolyether (PFPE) lubricants that have stability at temperatures from about 220 to about 350° C. PFPE lubricants include those available from DuPont (Wilmington, Del.) under the trademark Krytox®, such as the XHT series with thermal stability up to about 300 to 350° C. Other PFPE lubricants include those sold under the trademark Demnum™ from Daikin Industries (Japan) with thermal stability up to about 280 to 330° C., and available from Ausimont (Milan, Italy), under the trademarks Fomblin® and Galden® such as that available under the trademark Fomblin®-Y Fomblin®-Z with thermal stability up to about 220 to 260° C.

For high temperature condenser operation (associated with high temperature lifts and high compressor discharge temperatures) formulations of working fluid (e.g. HFO-153-10mzzy) and lubricants with high thermal stability (optionally in combination with oil cooling or other mitigation approaches) will be advantageous.

In one embodiment, the compositions may further comprise from about 0.01 weight percent to about 5 weight percent of a stabilizer, (e.g., a free radical scavenger, an acid scavenger or an antioxidant) to prevent degradation caused at high temperatures. Such other additives include but are not limited to, nitromethane, hindered phenols, hydroxylamines, thiols, phosphites, or lactones. Of note are compositions wherein the compositions comprise from about 0.1 weight percent to about 3 weight percent of a stabilizer. Single stabilizers or combinations may be used.

Optionally, in another embodiment, certain refrigeration, air-conditioning, or heat pump system additives may be added, as desired, to the working fluids as disclosed herein in order to enhance performance and system stability. These additives are known in the field of refrigeration and air-conditioning, and include, but are not limited to, anti-wear agents, extreme pressure lubricants, corrosion and oxidation inhibitors, metal surface deactivators, free radical scavengers, and foam control agents. In general, these additives may be present in the working fluids in small amounts relative to the overall composition. Typically concentrations of from less than about 0.1 weight percent to as much as about 3 weight percent of each additive are used. These additives are selected on the basis of the individual system requirements. These additives include members of the triaryl phosphate family of EP (extreme pressure) lubricity additives, such as butylated triphenyl phosphates (BTPP), or other alkylated triaryl phosphate esters, e.g. Syn-O-Ad 8478 from Akzo Chemicals, tricresyl phosphates and related compounds. Additionally, the metal dialkyl dithiophosphates (e.g., zinc dialkyl dithiophosphate (or ZDDP); Lubrizol 1375 and other members of this family of chemicals may be used in compositions of the present invention. Other anti-wear additives include natural product oils and asymmetrical polyhydroxyl lubrication additives, such as Synergol TMS (International Lubricants). Similarly, stabilizers such as anti-oxidants, free radical scavengers, and water scavengers may be employed. Compounds in this category can include, but are not limited to, butylated hydroxy toluene (BHT), epoxides, and mixtures thereof. Corrosion inhibitors include dodecyl succinic acid (DDSA), amine phosphate (AP), oleoyl sarcosine, imidazone derivatives and substituted sulfphonates. Metal surface deactivators include areoxalyl bis (benzylidene) hydrazide (CAS reg no. 6629-10-3), N,N'-bis (3,5-di-tert-butyl-4-hydroxyhydrocinnamoylhydrazine (CAS reg no. 32687-78-8), 2,2',-oxamidobis-ethyl-(3,5-di-tert-butyl-4-hydroxyhydrocinnamate (CAS reg no. 70331-94-1), N,N'-(disalicyclidene)-1,2-diaminopropane (CAS reg no. 94-91-7) and ethylenediaminetetra-acetic acid (CAS reg no. 60-00-4) and its salts, and mixtures thereof.

Of note are stabilizers to prevent degradation at temperatures of 55° C. or above. Also of note are stabilizers to prevent degradation at temperatures of 75° C. or above. Also of note are stabilizers to prevent degradation at temperatures of 85° C. or above. Also of note are stabilizers to prevent degradation at temperatures of 100° C. or above. Also of note are stabilizers to prevent degradation at temperatures of 139° C. or above. Also of note are stabilizers to prevent degradation at temperatures of 145° C. or above. Also of note are stabilizers to prevent degradation at temperatures of 155° C. or above. Also of note are stabilizers to prevent degradation at temperatures of 165° C. or above. Also of note are stabilizers to prevent degradation at temperatures of 170° C. or above. Also of note are stabilizers to prevent degradation at temperatures of 200° C. or above. Also of note are stabilizers to prevent degradation at temperatures of 250° C. or above.

Of note are stabilizers comprising at least one compound selected from the group consisting of hindered phenols, thiophosphates, butylated triphenylphosphorothionates, organo phosphates, or phosphites, aryl alkyl ethers, terpenes, terpenoids, epoxides, fluorinated epoxides, oxetanes, ascorbic acid, thiols, lactones, thioethers, amines, nitromethane, alkylsilanes, benzophenone derivatives, aryl sulfides, divinyl terephthalic acid, diphenyl terephthalic acid, ionic liquids, and mixtures thereof. Representative stabilizer compounds include but are not limited to tocopherol; hydroquinone; t-butyl hydroquinone; monothiophosphates; and dithiophosphates, commercially available from Ciba Specialty Chemicals, Basel, Switzerland, hereinafter "Ciba," under the trademark Irgalube® 63; dialkylthiophosphate esters, commercially available from Ciba under the trademarks Irgalube® 353 and Irgalube® 350, respectively; butylated triphenylphosphorothionates, commercially available from Ciba under the trademark Irgalube® 232; amine phosphates, commercially available from Ciba under the trademark Irgalube® 349 (Ciba); hindered phosphites, commercially available from Ciba as Irgafos® 168; a phosphate such as (Tris-(di-tert-butylphenyl), commercially available from Ciba under the trademark Irgafos® OPH; (Di-n-octyl phosphite); and iso-decyl diphenyl phosphite, commercially available from Ciba under the trademark Irgafos® DDPP; anisole; 1,4-dimethoxybenzene; 1,4-diethoxybenzene; 1,3,5-trimethoxybenzene; d-limonene; retinal; pinene; menthol; Vitamin A; terpinene; dipentene; lycopene; beta carotene; bornane; 1,2-propylene oxide; 1,2-butylene oxide; n-butyl glycidyl ether; trifluoromethyloxirane; 1,1-bis(trifluoromethyl)oxirane; 3-ethyl-3-hydroxymethyl-oxetane, such as OXT-101 (Toagosei Co., Ltd); 3-ethyl-3-((phenoxy) methyl)-oxetane, such as OXT-211 (Toagosei Co., Ltd); 3-ethyl-3-((2-ethyl-hexyloxy)methyl)-oxetane, such as OXT-212 (Toagosei Co., Ltd); ascorbic acid; methanethiol (methyl mercaptan); ethanethiol (ethyl mercaptan); Coenzyme A; dimercaptosuccinic acid (DMSA); grapefruit mercaptan ((R)-2-(4-methylcyclohex-3-enyl)propane-2-thiol)); cysteine ((R)-2-amino-3-sulfanyl-propanoic acid); lipoamide (1,2-dithiolane-3-pentanamide); 5,7-bis(1,1-dimethylethyl)-3-[2,3 (or 3,4)-dimethylphenyl]-2(3H)-benzofuranone, commercially available from Ciba under the trademark Irganox® HP-136; benzyl phenyl sulfide; diphenyl sulfide; diisopropylamine; dioctadecyl 3,3'-thiodipropionate, commercially available from Ciba under the trademark Irganox® PS 802 (Ciba); didodecyl 3,3'-thiopropionate, commercially available from Ciba under the trademark Irganox® PS 800; di-(2,2,6,6-tetramethyl-4-piperidyl)sebacate, commercially available from Ciba under the trademark Tinuvin® 770; poly-(N-hydroxyethyl-2,2,6,6-tetramethyl-4-hydroxy-piperidyl succinate, commercially available from Ciba under the trademark Tinuvin® 622LD (Ciba); methyl bis tallow amine; bis tallow amine; phenol-alpha-naphthylamine; bis(dimethylamino)methylsilane (DMAMS); tris(trimethylsilyl)silane (TTMSS); vinyltriethoxysilane; vinyltrimethoxysilane; 2,5-difluorobenzophenone; 2',5'-dihydroxyacetophenone; 2-aminobenzophenone; 2-chlorobenzophenone; benzyl phenyl sulfide; diphenyl sulfide; dibenzyl sulfide; ionic liquids; and others.

Also of note are ionic liquid stabilizers comprising at least one ionic liquid. Ionic liquids are organic salts that are liquid or have melting points below 100° C. In another embodiment, ionic liquid stabilizers comprise salts containing cations selected from the group consisting of pyridinium, pyridazinium, pyrimidinium, pyrazinium, imidazolium, pyrazolium, thiazolium, oxazolium and triazolium; and anions selected from the group consisting of [$BF_4$]-, [$PF_6$]-, [$SbF_6$]-, [$CF_3SO_3$]--, [$HCF_2CF_2SO_3$]-, [$CF_3HFCCF_2SO_3$]-, [$HCCIFCF_2SO_3$]-, [($CF_3SO_2$)$_2N$]—, [($CF_3CF_2SO_2$)$_2N$]—, [($CF_3SO_2$)$_3C$]—, [$CF_3CO_2$]-, and F—. Representative ionic liquid stabilizers include emim $BF_4$ (1-ethyl-3-methylimidazolium tetrafluoroborate); bmim $BF_4$ (1-butyl-3-methylimidazolium tetraborate); emim $PF_6$ (1-ethyl-3-methylimidazolium hexafluorophosphate); and bmim $PF_6$ (1-butyl-3-methylimidazolium hexafluorophosphate), all of which are available from Fluka (Sigma-Aldrich).

EXAMPLES

The concepts described herein will be further described in the following examples, which do not limit the scope of the invention described in the claims.

Example 1

Chemical Stability of HFO-153-10Mzzy at High Temperatures

The thermal stability of HFO-153-10mzzy was assessed through testing in sealed glass tubes according to the methodology of ANSI/ASHRAE Standard 97-2007. Samples of HFO-153-10mzzy were placed in glass tubes with immersed coupons of metals (Fe, Al, Cu, Stainless Steel 304) commonly used in the construction of heat pumps and other equipment. The tubes were sealed and heated in an oven at 175° C. for 32 days. The decomposition of HFO-153-10mzzy after aging for 32 days was quantified in terms of the measured fluoride ion concentration in parts per million (ppm). The concentration of fluoride ion resulting from the degradation of HFO-153-10mzzy was less than 100 ppm indicating good thermal stability. HFO-153-10mzzy, despite its unsaturated chemical nature, exhibited thermal stability similar to Novec® HFE-7100, as shown in Table 1 below.

TABLE 1

| Metal/Catalyst | HFO-153-10mzzy | Novec ® HFE-7100 |
| --- | --- | --- |
| Fe | 4.3 | 1.0 |
| Al | 2.0 | 6.8 |
| Cu | 1.3 | 4.5 |
| Stainless Steel 304 | 5.1 | 6.1 |

High thermal stability, non-flammability, low GWP, high critical temperature and low vapor pressure make HFO-153-10mzzy attractive as a working fluid in high temperature heat pumps.

Example 2

Heat Pump Performance with HFO-153 10Mzzy for Lifting Heat from 80° C. to 126° C.

Table 2 shows the performance data of a heat pump used to lift heat from 80° C. to 126° C. operating with HFO-153-10mzzy as the working fluid as compared to the performance data of a heat pump operationing with HFC-245fa as the working fluid. In addition to offering a significantly lower GWP, HFO-153-10mzzy realizes a 4.1% higher CORI. Moreover, the compressor discharge temperature with HFO-153-10mzzy is within the upper limit for most compressors while the compressor discharge temperature with HFC-245fa exceeds the upper limit for most compressors.

TABLE 2

|  |  | HFC-245fa | HFO-153 10mzzy | HFO-153 10mzzy vs. HFC-245fa % |
| --- | --- | --- | --- | --- |
| $T_{cr}$ | ° C. | 154 | 170.24 |  |
| $P_{cr}$ | MPa | 3.65 | 2.04 |  |
| $T_b$ | ° C. | 15.1 | 49 |  |
| $T_{evap}$ | ° C. | 80 | 80 |  |
| $T_{cond}$ | ° C. | 126 | 126 |  |
| Lift | ° C. | 46 | 46 |  |
| Suction Superheat | K | 25 | 25 |  |
| Liquid Subcooling | K | 15 | 15 |  |
| Compressor Efficiency |  | 0.7 | 0.7 |  |
| $P_{cond}$ | MPa | 2.17 | 0.84 |  |
| $T_{disch}$ | ° C. | 146.12 | 130.64 |  |
| $COP_h$ |  | 5.644 | 5.875 | +4.1 |

Example 3

Heat Pump Performance with HFO-153 10Mzzy for Lifting Heat from 90° C. to 145° C.

Table 3 shows the performance data of a heat pump used to lift heat from 90° C. to 145° C. operating with HFO-153-10mzzy as the working fluid as compared to the performance data of a heat pump used to lift heat from 90° C. to 126° C. operating with HFC-245fa as the working fluid. The maximum permissible working pressure for many heat pumps (e.g. commonly available centrifugal heat pumps) is about 2.18 MPa; it limits the condensing temperature with HFC-245fa to a maximum of about 126° C. The condensing pressure for the heat pump operated with HFO-153-10mzzy as the working fluid remains comfortably below the maximum permissible working pressure of 2.18 MPa even at the higher condensing temperature of 145° C. Moreover, the compressor discharge temperature with HFO-153-10mzzy remains below that with HFC-245fa even with the significantly higher temperature lift with HFO-153-10mzzy. Therefore, in addition to offering a significantly lower GWP than HFC-245fa, HFO-153-10mzzy could enable the realization of heat pumps achieving higher heating temperatures than HFC-245fa. It could also enable the retrofit of heat pumps originally design for HFC-245fa, so as to reduce the GWP of the working fluid while at the same time allowing higher heating temperatures.

TABLE 3

|  |  | HFC-245fa | HFO-1531 0mzzy |
|---|---|---|---|
| $T_{evap}$ | °C. | 90 | 90 |
| $T_{cond}$ | °C. | 126 | 145 |
| Lift | °C. | 36 | 55 |
| Suction Superheat | K | 35 | 35 |
| Liquid Subcooling | K | 15 | 15 |
| Compressor Efficiency |  | 0.7 | 0.7 |
| $P_{cond}$ | MPa | 2.17 | 1.26 |
| $T_{disch}$ | °C. | 156.78 | 155.93 |
| $COP_h$ |  | 7.656 | 4.951 |

What is claimed is:

1. A method for producing heating in a high temperature heat pump apparatus having a heat exchanger comprising extracting heat from a working fluid, thereby producing a cooled working fluid wherein said working fluid comprises (2E)-1,1,1,4,5,5,5-heptafluoro-4-(trifluoromethyl)pent-2-ene, wherein the heat exchanger operates at a temperature of at least about 55° C.

2. The method of claim 1 wherein the heat exchanger is selected from the group consisting of a supercritical working fluid cooler and a condenser.

3. The method of claim 1 further comprising passing a first heat transfer medium through the heat exchanger, whereby said extraction of heat heats the first heat transfer medium, and passing the heated first heat transfer medium from the heat exchanger to a body to be heated.

4. The method of claim 3, wherein the first heat transfer medium is an industrial heat transfer liquid and the body to be heated is a chemical process stream.

5. The method of claim 1 further comprising expanding the working fluid and then heating the working fluid in a second heat exchanger to produce a heated working fluid.

6. The method of claim 3 wherein said second heat exchanger is an evaporator and the heated working fluid is a vapor.

7. The method of claim 4, further comprising compressing the working fluid vapor in a dynamic or a positive displacement compressor.

8. The method of claim 5, wherein the dynamic compressor is a centrifugal compressor.

9. The method of claim 1 further comprising passing a fluid to be heated through said heat exchanger, thus heating the fluid.

10. The method of claim 1, wherein the high temperature heat pump apparatus is suitable for use with HFC-245fa.

11. A method of raising the maximum feasible condenser operating temperature to a temperature greater than about 127° C. in a high temperature heat pump apparatus comprising: charging the high temperature heat pump apparatus with a working fluid comprising (2E)-1,1,1,4,5,5,5-heptafluoro-4-(trifluoromethyl)pent-2-ene.

12. The method of claim 11, wherein the high temperature heat pump apparatus is suitable for use with HFC-245fa.

13. The method of claim 1, wherein the heat exchanger operates at a temperature of at least about 127° C.

14. The method of claim 1, wherein the heat exchanger operates at a temperature of at least about 155° C.

15. The method of claim 1, wherein the heat exchanger operates at a temperature from about 160° C. to about 169° C.

16. The method of claim 11 wherein the maximum feasible condenser operating temperature is raised to a temperature greater than about 155° C.

17. The method of claim 11 wherein the maximum feasible condenser operating temperature is raised to a temperature greater than about 160° C.

18. The method of claim 11 wherein the maximum feasible condenser operating temperature is raised to a temperature greater than about 168° C.

* * * * *